(12) United States Patent
Lunderqvist et al.

(10) Patent No.: US 7,189,253 B2
(45) Date of Patent: Mar. 13, 2007

(54) CEREBRAL TEMPERATURE CONTROL

(75) Inventors: Anders Lunderqvist, Lund (SE); Mats Aller, Lund (SE); Fredrik Boris-Möller, Lund (SE); Tadeusz Wielock, Lund (SE)

(73) Assignee: Quickcool AB (SE)

( * ) Notice: Subject to any disclaimer, the term of this patent is extended or adjusted under 35 U.S.C. 154(b) by 75 days.

(21) Appl. No.: 10/708,624

(22) Filed: Mar. 16, 2004

(65) Prior Publication Data
US 2005/0209662 A1    Sep. 22, 2005

(51) Int. Cl.
*A61F 7/00* (2006.01)
(52) U.S. Cl. .................. 607/105; 607/104; 607/113
(58) Field of Classification Search ............... 607/96, 607/104–107, 113–114
See application file for complete search history.

(56) References Cited

U.S. PATENT DOCUMENTS

| 4,949,718 A * | 8/1990 | Neuwirth et al. ............. 607/27 |
| 5,257,977 A * | 11/1993 | Eshel ........................ 604/113 |
| 5,324,392 A * | 6/1994 | Tate et al. ................... 162/348 |
| 6,647,930 B2 * | 11/2003 | Nurmi ......................... 122/4 R |
| 6,758,857 B2 * | 7/2004 | Cioanta et al. ............. 607/105 |
| 2002/0151943 A1 * | 10/2002 | Balding ....................... 607/105 |
| 2004/0138728 A1 * | 7/2004 | Wong et al. ................ 607/105 |
| 2004/0210281 A1 * | 10/2004 | Dzeng et al. ................. 607/96 |

* cited by examiner

*Primary Examiner*—Roy D Gibson
(74) *Attorney, Agent, or Firm*—Ostrolenk, Faber, Gerb & Soffen, LLP (57) ABSTRACT

A system (10) for cerebral temperature control of a living being, comprising a double lumen catheter means (30) configured to be introduced through a nostril of a living being and to be placed with its tip at the level of the back of the tongue. The double lumen catheter means (30) comprises a first lumen (32) and a second lumen (38), said first and second lumens are in fluid communication by means of a set of end openings (34), said second lumen being configured as an expandable balloon. Further comprising a temperature regulator (24) connected to a reservoir (20) comprising a fluid (22), said temperature regulator being configured to regulate the temperature of said fluid, and means (12, 14, 16) for circulating said temperature regulated fluid from said reservoir into said first lumen, from said first lumen into said second lumen, and from said second lumen back to said reservoir.

30 Claims, 7 Drawing Sheets

CEREBRAL TEMPERATURE CONTROL

BACKGROUND OF INVENTION

1. Technical Field of the Invention

The present invention refers to the control of the temperature of the brain of a living being, and especially to cooling of the brain.

In pathological conditions, the body temperature or the temperature of the body parts of a living being influences the healing process and the risk of permanent damage. Cancer cells, for example, are heat sensitive and a local heating of the blood flow around a cancer tumor may for some types of cancer constitute a treatment resulting in restrained tumor growth or in some cases even in a shrinking of the tumor. In other cases cooling of a body part may be important to reduce adverse secondary symptoms of the pathological condition.

In the case of a stroke, the blood flow to the brain is reduced (ischemia) due to a hemorrhage or the clogging of a blood vessel. This condition will cause permanent functional deficits unless treatment to restore blood flow and protect nerve cells is initiated at an early stage, which will reduce the loss of bodily functions, such as paralysis. It is well known that cooling the brain effectively blocks the development of cellular damage after an episode of ischemia. Cooling of the patient suffering transient circulatory arrest to the brain results in a reduction of the symptoms of neurological deficit. However, there are certain problems associated with whole body cooling. One is that the cooling is not fast enough to effectively use its protective potential. Another problem is that whole body cooling must be carried out under close control of physiological parameters or under anesthesia. Yet another problem is that there is a risk of cardiovascular complications.

In the case of a circulatory arrest, the brain can suffer permanent damage if the arrest exceeds a time period of about 5–15 minutes. However, if the temperature of the brain is lowered before or after the arrest the brain damage is diminished.

In the case of brain trauma the brain suffers from open or close head concussion. Hypothermia has been shown to diminish traumatic brain injury in such cases.

There are several methods in the prior art to carry out a more isolated cooling of a single organ or body part. An example of cooling of the brain in a human being is disclosed in the patent document WO 98/23217, relating to a method of cerebral retro-perfusion and retro-infusion, involving the cooling of arterial blood that then is returned to the entire brain. However, this method entails a large and complicated surgical procedure, which delays the inset of an actual treatment.

The U.S. Pat. No. 5,906,588 discloses a method and a device for heart-lung bypass and cooling of a specific body part. This disclosure primarily relates to complicated heart surgery and organ transplantation.

The U.S. patent application Ser. No. 10/072,857 discloses a first phase comprising the step of introducing an infusion catheter for infusion of a temperature controlled infusion solution or perfusate into a vein initiating quick general body hypothermia. An optional second phase, wherein a second infusion catheter is introduced into an artery of the living being, the second infusion catheter being configured to provide selective temperature control of the brain and infusion of other important substrates and pharmacological compounds into the brain. A third phase is also disclosed, wherein an extra-corporeal circuit is established between a vein and an artery. Blood is withdrawn from the vein, the temperature of the blood is modified outside the body and the blood is returned to the body through the artery.

2. Purpose of the Invention

A purpose of the present invention is to provide a system and a method for quick and efficient control of the temperature of the brain without changing the temperature of the rest of the body. An aim of the invention is to provide a system and a method that is simple and initially does not require specialized personnel acquainted with for example radiology or other diagnostic imaging techniques.

SUMMARY OF INVENTION

The above-mentioned purpose and aim, amongst others, are fulfilled by means of a system, a method, a special designed catheter means and a kit of disposables according to the independent claims. Further embodiments of the invention are defined in the dependent claims.

By means of the present invention, the naso-pharyngeal membranes can be temperature regulated, e.g. cooled or heated, whereby the cold or heat is transmitted to the adjacent arterial and venous structures, which in turn is transmitting the cold or heat to the brain. In this way, the temperature of the brain parenchyma can be reduced or increased without any direct contact with vascular system.

BRIEF DESCRIPTION OF DRAWINGS

The present invention will be described with reference to the accompanying drawings, in which.

DETAILED DESCRIPTION

Figure 1:
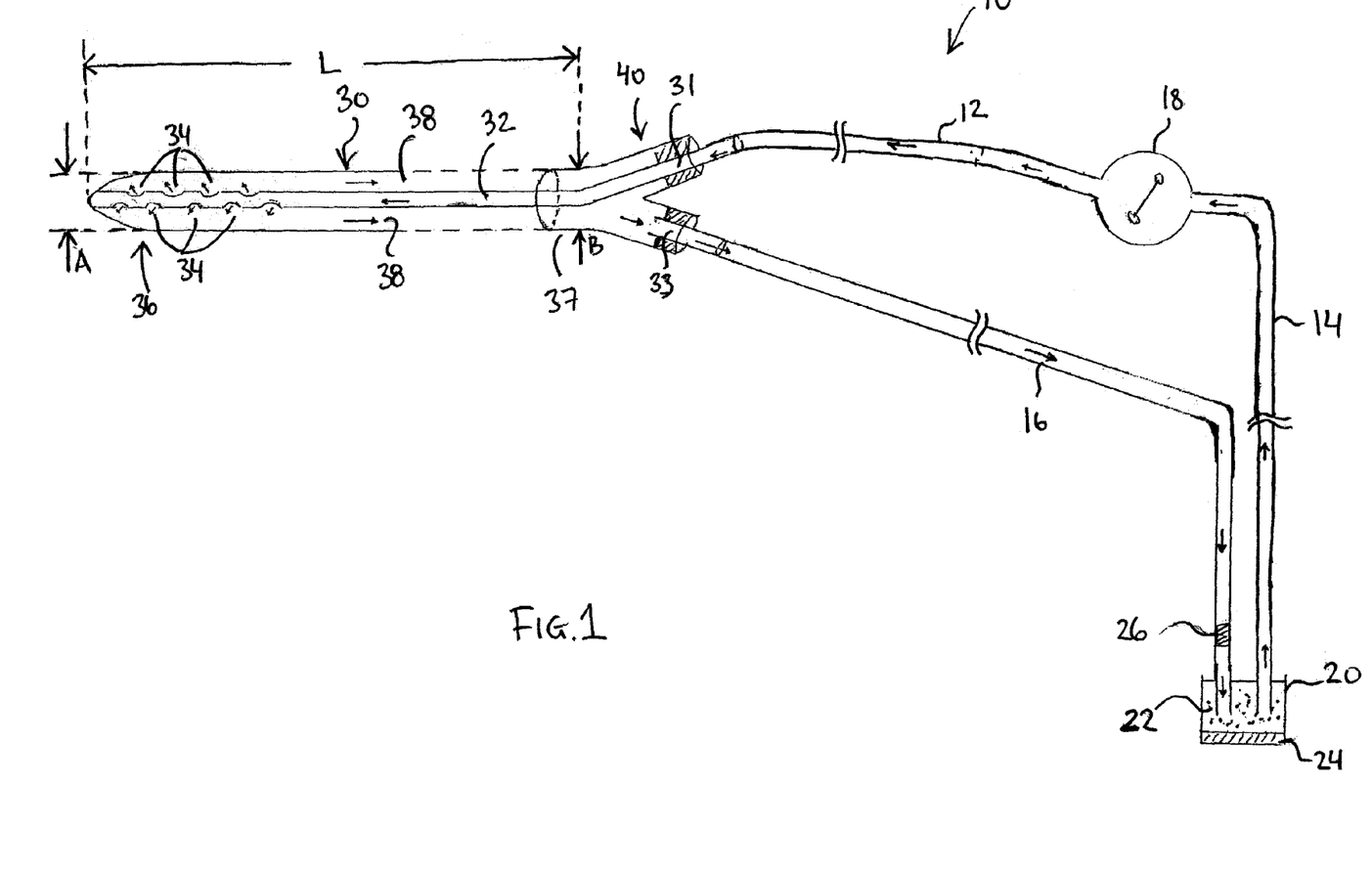
FIG. 1 schematically shows a first embodiment of a system according to the present invention.
Figure 2:
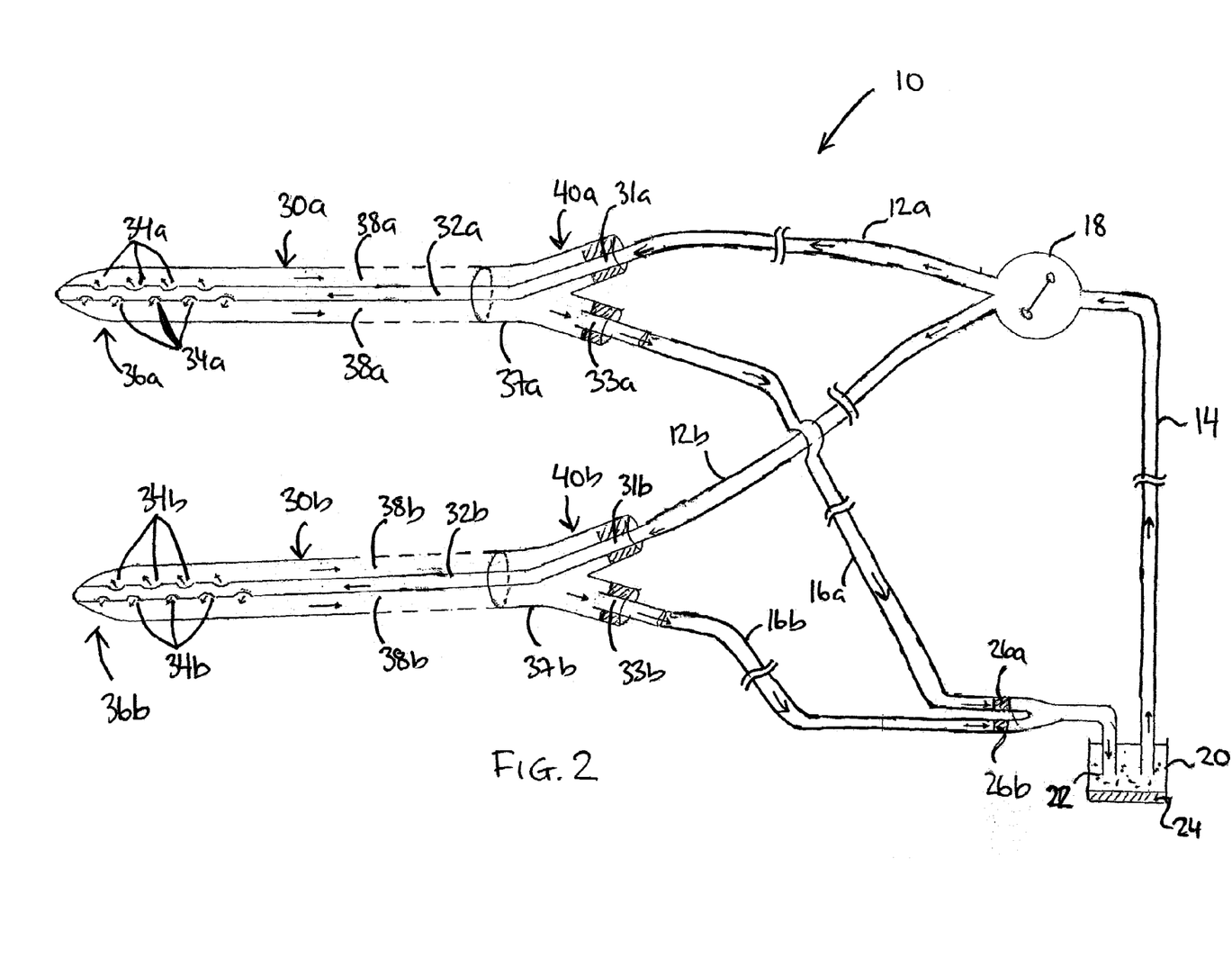
FIG. 2 schematically shows a second embodiment of a system according to the present invention.

The present invention will now be described with reference to the accompanying figures. FIG. 1 shows a first embodiment of an inventive system 10 for cerebral temperature control of a living being, in which embodiment the system comprises one double lumen catheter. FIG. 2 shows schematically a second embodiment of the inventive system, which system comprises two double lumen catheters to be introduced in respective nostril of a living being. By means of two catheter means, the temperature regulation is accomplished more effectively and quicker.

In the figures, the same reference numerals are used to indicated corresponding components. Further, in FIG. 2, the corresponding components and details of the respective catheter means are distinguished by means of the addition of the letter a respective b to the reference numeral. Arrows are used to show the flow direction of the fluid in the system.

However, as understood by the skilled person the fluid flow can have the opposite direction to that indicated in the figures.

Figure 3:
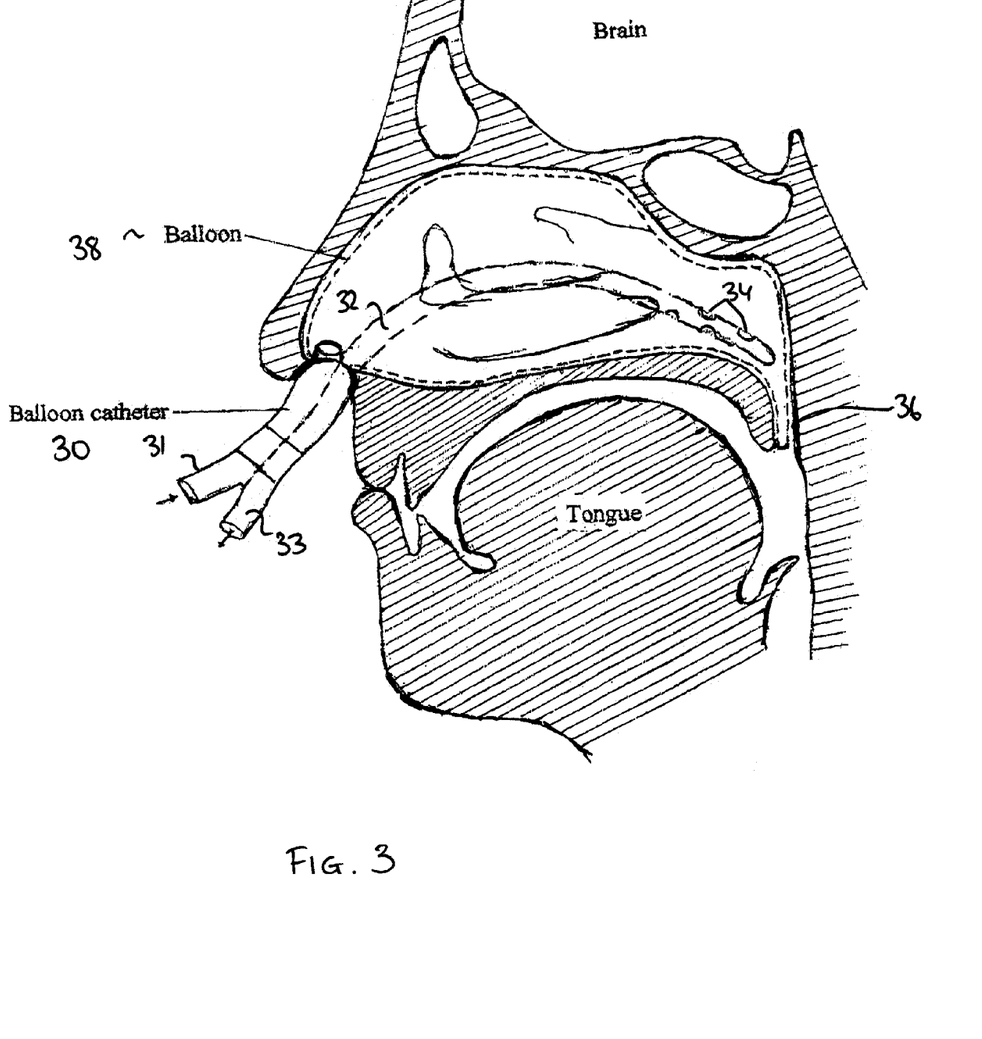
FIG. 3 schematically shows a side view of the double lumen catheter means arranged at the inner surface of the nose and epipharynx of a patient.

The system 10 comprises a double lumen balloon catheter means 30, 30a, 30b configured to be introduced through a nostril of a living being and to be placed with its tip at the level of the back of the tongue, cf. FIG. 3.

The double lumen balloon catheter means 30, 30a, 30b comprises a first lumen 32, 32a, 32b and a second lumen 38, 38a, 38b. The first and second lumens 32, 38 are arranged in fluid communication by means of a set of end openings 34, 34a, 34b. The second lumen 38 is configured as an expandable balloon 38.

The system 10 comprises further a temperature regulator 24 connected to a reservoir 20 comprising a fluid 22. The temperature regulator 24 is configured to regulate the temperature of the fluid 22 comprised in the reservoir. The fluid 22 is for example a saline solution. Means 12, 12a, 12b, 14, 16, 16a, 16b for circulating said temperature regulated fluid 22 from the reservoir 20 to the catheter means 30, 30a, 30b are also provided. The means 12, 12a, 12b, 14, 16, 16a, 16b are configured to circulate the fluid 22 into the first lumen 32, 32a, 32b of the catheter means 30, 30a, 30b, from the first lumen 32, 32a, 32b into the second lumen 38, 38a, 38b, and from the second lumen 38, 38a, 38b back to said reservoir 20.

The means 12, 12a, 12b, 14, 16, 16a, 16b for circulating said temperature regulated fluid 22 comprises a set of tubings 12, 12a, 12b, 14, 16, 16a, 16b configured to connect the catheter means 30, 30a, 30b to the reservoir 20.

In use, when the fluid enters the second catheter 38, 38a, 38b, the second catheter means 38, 38a, 38b is expanded as a balloon to completely or almost completely cover the inner surface of the nose and epipharynx, whereby the nasopharyngeal membranes is temperature regulated, cf. FIG. 3. The temperature is transferred to adjacent arterial and venous structures, which are transferring the temperature to the brain.

Further, by means of the inventive arrangement the temperature regulated fluid 22 circulates in a closed fluid system 12, 12a, 12b, 14, 16, 16a, 16b, 30a, 30b, 20.

The inventive double lumen balloon catheter means 30, 30a, 30b comprises an inlet 31, 31a, 31b arranged to provide fluid communication with the reservoir 20 and with the first lumen 32, 32a, 32b. The inlet 31, 31a, 31b is further configured to receive an amount of the temperature regulated fluid 22 from the reservoir 20. The first lumen 32, 32a, 32b has a set of distal end openings 34, 34a, 34b in a front end portion 36, 36a, 36b of the catheter means 30, 30a, 30b. The end openings 34, 34a, 34b being arranged to provide fluid communication with said second lumen 38, 38a, 38b. The catheter means 30, 30a, 30b further comprises an outlet 33, 33a, 33b configured to provide fluid communication with the second lumen 38, 38a, 38b and with the reservoir 20.

The inlet 31, 31a, 31b and the outlet 33, 33a, 33b being arranged at an end portion 40, 40a, 40b of the catheter means 30, 30a, 30b.

According to an embodiment, the catheter means 30, 30a, 30b has a length L of approximately 20–25 cm. In expanded state, the diameter A of the catheter means at a front part 36, 36a, 36b of the catheter means is approximately 2–4 cm and the diameter B of the catheter means at a base part 37, 37a, 37b of the catheter means is approximately 1–3 cm, but these figures can be exceeded if balloon pressure is increased.

According to an embodiment of the invention, the circulation of the fluid 22 is accomplished by means of the hydrostatic pressure of the fluid 22 in the reservoir 20. However, according to another embodiment of the invention, the means 12, 14, 16 for circulating the temperature regulated fluid 22 further comprises a pumping means 18 arranged between the reservoir 20 and the catheter means 30, 30a, 30b by means of tubings 12, 12a, 12b, 14. Thus, it should be understood that the pumping means 18 illustrated in FIGS. 1 and 2 is optional.

The circulation means for circulating the fluid is preferably configured to provided a fluid flow rate of 200–1000 ml/min.

The inventive system can also comprise a pressure regulating nozzle 26, 26a, 26b arranged at the tubings 16, 16a, 16b. The pressure regulating nozzle 26, 26a, 26b is arranged close to the reservoir 20 and being configured to provide a resistance in the tubings, whereby the fluid flowing in the system is able to expand the double lumen catheter means (cf. FIG. 3).

Figure 5:
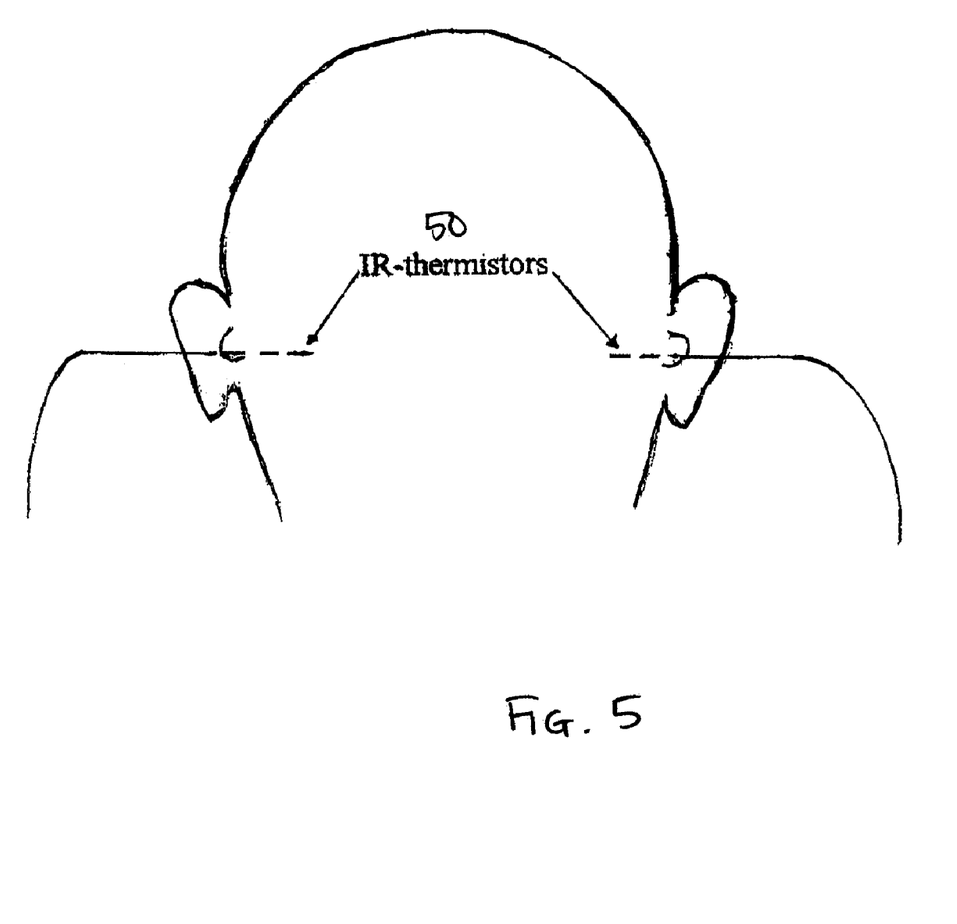
FIG. 5 schematically shows two temperature sensors, each of which is arranged in an auditory canal.

The system can also comprise a temperature sensor 50 (cf. FIG. 5) configured to be arranged in an auditory canal of the living being. The temperature sensor is connectable to the temperature regulator 24, configured to register the temperature of the brain and to automatically control the temperature regulator 24 to regulate the temperature of the fluid in the reservoir 20 in order to maintain the temperature of the brain at a desired level. The temperature sensor is for example an IR thermistor and the desired brain temperature level is approximately 31–32 degrees Celsius.

The present invention also relates to a double lumen balloon catheter means 30, 30a, 30b. The catheter means 30, 30a, 30b is configured to be introduced through a nostril of a living being and to be placed with its tip at the level of the back of the tongue. The catheter means 30, 30a, 30b comprises a first lumen 32, 32a, 32b and a second lumen 38, 38a, 38b. The first and second lumens 32, 32a, 32b, 38, 38a, 38b are configured to be in fluid communication by means of a set of end openings 34, 34a, 34b. The second lumen 38, 38a, 38b being configured as an expandable balloon 38.

The catheter means 30, 30a, 30b further comprises an inlet 31, 31a, 31b arrangeable in fluid communication with a reservoir 20 and with the first lumen 32, 32a, 32b. The inlet 31, 31a, 31b is further configured to receive a fluid 22 from the reservoir 20. The first lumen 32, 32a, 32b has a set of distal end openings 34, 34a, 34b in a front end portion 36, 36a, 36b of the catheter means 30, 30a, 30b, which end openings 34, 34a, 34b being arrangeable in fluid communication with the second lumen 38, 38a, 38b. The catheter means 30, 30a, 30b further comprises an outlet 33, 33a, 33b arrangeable in fluid communication with the second lumen 38, 38a, 38b and with the reservoir 20.

The inlet 31, 31a, 31b and outlet 33, 33a, 33b are preferably arranged at an end portion 40, 40a, 40b of the catheter means 30, 30a, 30b.

The catheter means 30, 30a, 30b is for example manufactured of a flexible material such as plastic, synthetic latex, silicone or Gore-Tex.

The present invention also relates to a kit of disposables for use in the inventive system. The kit comprises a plurality of tubings, and the double lumen balloon catheter means 30.

The invention relates also to a method for cerebral temperature control. The method comprises the steps of:

100 introducing a double lumen balloon catheter means through a nostril of a living being;

102 placing said catheter means with its tip at the level of the back of the tongue;

104 temperature regulating a fluid in a reservoir;

106 circulating said temperature regulated fluid from said reservoir into a first lumen of said catheter means, from said first lumen into a second lumen of said catheter means, and from said second lumen back to said reservoir, whereby the balloon is expanded to completely cover the inner surface of the nose and epipharynx and whereby said temperature regulated fluid circulates in a closed fluid system.

The step 106 of circulating said temperature regulated fluid comprises the step of pumping said fluid from said reservoir, to said catheter means and back to said reservoir via said first and second lumens by means of a pumping means.

The temperature regulated fluid circulates at a flow rate in the interval of approximately 200–1000 ml/min.

The method can further comprise the steps of placing a temperature sensor in an auditory canal of the living being, of registering the brain temperature by means of said temperature sensor and of temperature regulating the fluid in dependence of said registered brain temperature in order to maintain the brain temperature at a desired level.

The step of temperature regulating said fluid comprises the step of cooling said fluid in order to obtain a brain temperature of approximately 31–32 degrees Celsius.

Figure 4:
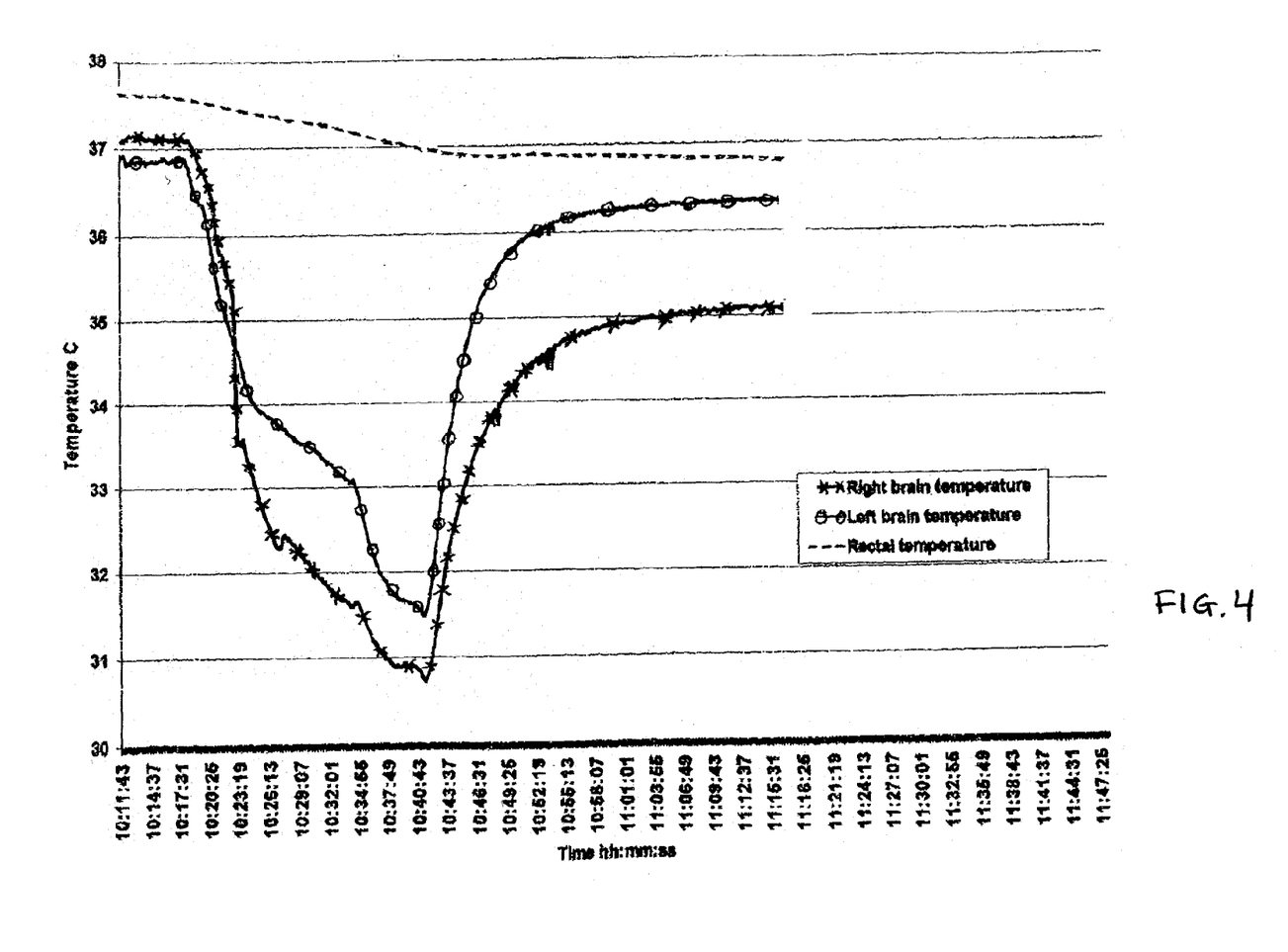
FIG. 4 shows an example of the registered temperature variation in the brain as a function of the time, when the inventive system and method is applied to a laboratory animal in the form of a pig.

FIG. 4 schematically shows how the registered temperature in the left and right brain hemisphere dramatically is reduced after the onset of the inventive method, while the registered temperature in the rectum remains almost unchanged. In the performed experiment, a double lumen catheter means was introduced in respective nostril of the pig. The temperature regulator cooled the fluid. Circulation of cold fluid started approximately at 10:18 and stopped approximately at 10:41. As seen from FIG. 4 the registered temperature in the left and right brain hemisphere is dramatically reduced within a short period of time after the start and increases again after the stop. Further, the temperature of the rectum is almost unchanged. Thus, a selectively cooling of the brain is accomplished.

Figure 6A:
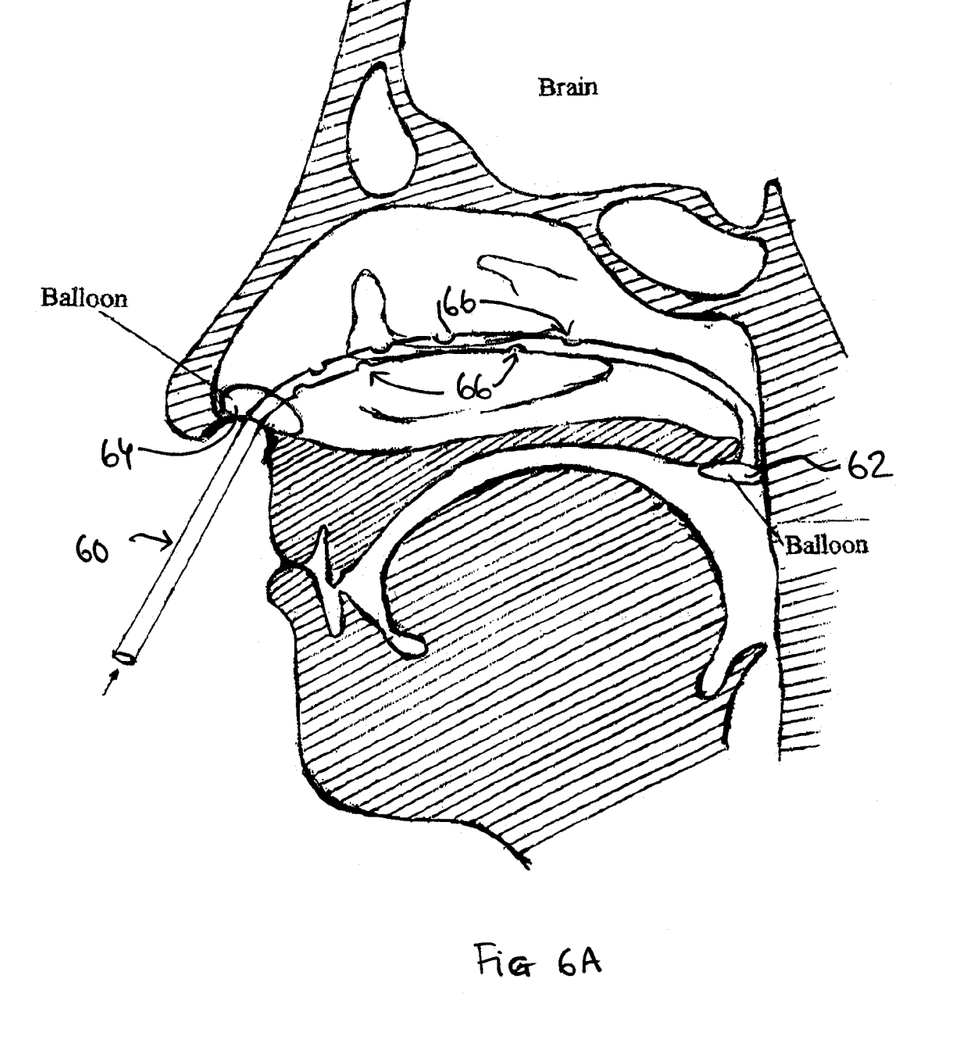
FIGS. 6A and 6B schematically shows side views of a third embodiment of a system according to the present invention.
Figure 6B:
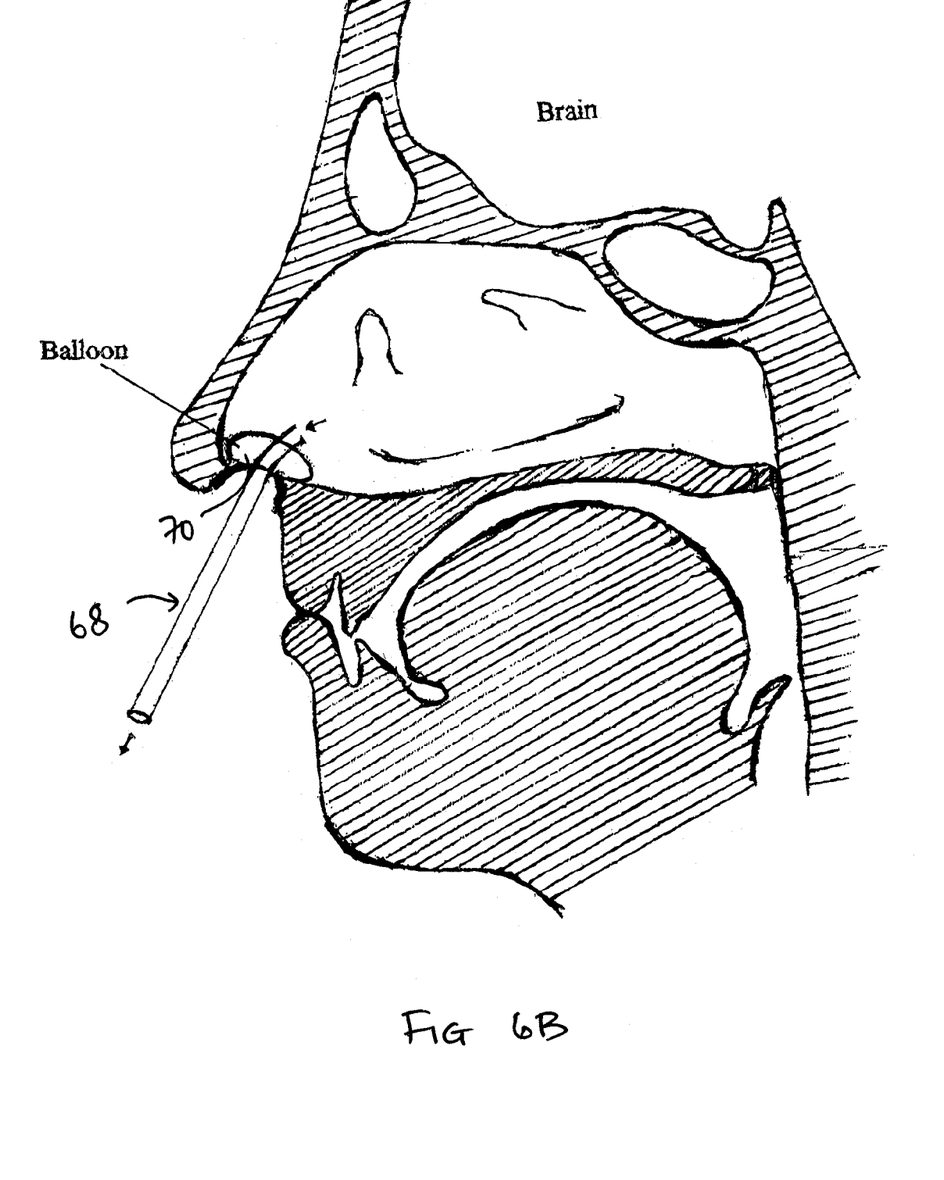

The present invention has been described with reference to embodiments and an example. However, it should be understood that modifications of components or functional steps can be performed without falling outside the scope of the invention. As an example, another embodiment of the invention will now be described with reference to FIGS. 6A and 6B. A double balloon catheter 60 (cf. FIG. 6A) is introduced through one nostril. The inner balloon 62, when expanded, fixates the soft palatinum and occludes the entrance to the mouth. The second balloon 64 is configured to occlude the nostril. A second balloon catheter 68 (cf. FIG. 6B) is placed into the other nostril, the second balloon catheter 68 having a balloon 70 configured to occlude the nostril. A temperature regulated fluid, e.g. cold saline, is injected into the first catheter 60 and leaves through side holes 66 arranged between the balloons 62, 64 of the first catheter 60. The cold saline flushes the cavum nasae and epipharynx and leaves through the other nostril, whereby the naso-pharyngeal membranes is temperature regulated. It should be understood that the pumping means, tubings, fluid reservoir, temperature regulated means or other elements described above can be used in this embodiment.

The invention claimed is:

1. A system for cerebral temperature control of a living being, comprising:
a first double lumen balloon catheter configured to be introduced through a nostril of a living being; said double lumen balloon catheter comprising:
a first lumen and a second lumen, said first and second lumens being in fluid communication by means of respective openings, said second lumen being configured as an expandable first balloon;
a second double lumen balloon catheter configured to be introduced through another nostril of said living being; said second double lumen balloon catheter comprising a third lumen and a fourth lumen, said third and fourth lumens being in fluid communication by means of respective openings, said fourth lumen being configured as an expandable second balloon;
a temperature regulator connected to a reservoir comprising a fluid, said temperature regulator being configured to regulate the temperature of said fluid;
a circulation mechanism operative to pass said temperature regulated fluid to each of said first and second catheters from said reservoir into said first lumen, from said first lumen into said second lumen, and out from said second lumen, and from said reservoir into said third lumen, from said third lumen into said fourth lumen, and out from said fourth lumen,
whereby said first and second balloons, when in use, are expandable to cover the inner surfaces of the nose.

2. The system of claim 1, wherein said temperature regulated fluid is circulated in a closed fluid system.

3. The system of claim 1, wherein said circulation of said fluid is accomplished by the hydrostatic pressure of said fluid in said reservoir.

4. The system of claim 1, wherein said circulation mechanism further comprises a pump connected by tubing between said reservoir and said catheters.

5. The system of claim 1, wherein said circulation mechanism is configured to provided a flow rate of 200–1000 ml/min.

6. The system of claim 1, further comprising a pressure regulating nozzle located in the tubing at the reservoir, said pressure regulating nozzle being configured to provide a resistance in the tubing.

7. The system of claim 6, wherein the pressure regulating nozzle is arranged for providing a resistance in the tubing for expanding the double lumen catheter.

8. The system of claim 1, further comprising a temperature sensor positionable in an auditory canal of a living being, to provide an estimate of the temperature of the brain and to control the temperature regulator to regulate the temperature of the fluid in the reservoir.

9. The system of claim 8, wherein said temperature sensor is an IR thermistor positionable in the auditory canal of the living being.

10. The system of claim 8, wherein said desired brain temperature level is approximately 31–32 degrees Celsius.

11. The system of claim 1, wherein said catheters are manufactured of a material selected from the group comprising plastic, synthetic latex, silicone and Gore-Tex®.

12. The system of claim 1, wherein said double lumen balloon catheters have a length of approximately 20 to 25 cm.

13. The system of claim 1, wherein said double lumen balloon catheters have a diameter at a front part of approximately 2 to 4 cm.

14. The system of claim 1, wherein said double lumen balloon catheter have a diameter at a base part of approximately 1 to 3 cm.

15. The system of claim 1, wherein said first double lumen balloon catheter is configured to be introduced through the nostril of a living being to a position which is not further than adjacent the level of the back of the tongue.

16. The system of claim 1, wherein said second double lumen balloon catheter is configured to be introduced through the nostril of a living being to a position which is not further than adjacent the level of the back of the tongue.

17. The system of claim 1, wherein said circulation mechanism comprises tubing connecting said catheters to said reservoir.

18. The system of claim 17, wherein each of said double lumen balloon catheters comprises:
- an inlet in fluid communication with said reservoir and with said first lumen, said inlet being configured to receive said fluid from said reservoir;
- said first lumen having a set of distal end openings in a front end portion of said first catheter said end openings being arranged in fluid communication with said second lumen; and
- an outlet in fluid communication with said second lumen and with said reservoir.

19. The system of claim 18, wherein said inlet and outlet are arranged at an end portion of said first catheter.

20. A kit of disposables comprising:
- two replacement double lumen balloon catheters for use in the system according to any of the claims 1, 2, 18–11, 12–14, 7 and 17; and
- tubing configured for connecting the catheters to said reservoir,
- said catheters and said tubing being disposable after use.

21. A method for cerebral temperature control, comprising the steps of:
- introducing a double lumen balloon catheter through a nostril of a living being;
- placing said catheter adjacent the level of the back of the tongue;
- regulating the temperature of a fluid in a reservoir;
- circulating said temperature regulated fluid from said reservoir into a first lumen of said catheter from said first lumen into a second lumen of said catheter and from said second lumen back to said reservoir,
- whereby the balloon is expanded to cover the inner surface of the nose.

22. The method of claim 21, wherein said step of circulating said temperature regulated fluid comprises the step of pumping said fluid from said reservoir to said catheter and back to said reservoir via said first and second lumens by a pump.

23. The method claim 21, wherein said temperature regulated fluid circulates at a flow rate in the range of approximately 200–1000 ml/min.

24. The method of claim 21, further comprising the steps of:
- placing a temperature sensor in an auditory canal of the living being;
- estimating the brain temperature by means of said temperature sensor; and
- regulating the temperature the fluid in dependence of said estimated brain temperature.

25. The method of claim 24, wherein the step of regulating the temperature of the fluid comprises the step of cooling said fluid in order to obtain a brain temperature of approximately 31–32 degrees Celsius.

26. The method of claim 21, wherein said double lumen balloon catheter has a length of approximately 20 to 25 cm.

27. The method of claim 21, wherein said double lumen balloon catheter has a diameter at a front part of approximately 2 to 4 cm.

28. The method of claim 21, wherein said double lumen balloon catheter has a diameter at a base part of approximately 1 to 3 cm.

29. The method of claim 21, further comprising:
- circulating the temperature regulated fluid through a system of tubing; and
- regulating fluid pressure in the tubing by a pressure regulating nozzle located in the tubing at the reservoir, for providing a resistance in the tubing.

30. The method of claim 21, further comprising:
- regulating a pressure of the circulating fluid by a pressure regulating nozzle for expanding the double lumen catheter.

* * * * *

UNITED STATES PATENT AND TRADEMARK OFFICE
CERTIFICATE OF CORRECTION

PATENT NO. : 7,189,253 B2  Page 1 of 1
APPLICATION NO. : 10/708624
DATED : March 13, 2007
INVENTOR(S) : Anders Lunderqvist et al.

It is certified that error appears in the above-identified patent and that said Letters Patent is hereby corrected as shown below:

On title page Item [75] Insert
(75) Inventors: Anders Lunderqvist, Lund (SE); Mats Allers, Lund (SE); Fredrik Boris-Möller, Lund (SE); Tadeusz Wielock, Lund (SE).

Signed and Sealed this

First Day of May, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,189,253 B2 |
| APPLICATION NO. | : 10/708624 |
| DATED | : March 13, 2007 |
| INVENTOR(S) | : Anders Lunderquist |

It is certified that error appears in the above-identified patent and that said Letters Patent is hereby corrected as shown below:

On the title page [75] insert:

(75) Inventors: Anders Lunderquist, Lund (SE); Mats Allers, Lund (SE); Fredrik Boris-Möller, Lund (SE); Tadeusz Wieloch, Lund (SE).

Signed and Sealed this

Sixth Day of November, 2007

JON W. DUDAS
*Director of the United States Patent and Trademark Office*